United States Patent
Chen et al.

(10) Patent No.: US 11,996,195 B2
(45) Date of Patent: May 28, 2024

(54) TRAINING DATA PROCESSING METHOD AND ELECTRONIC DEVICE

(71) Applicants: Acer Incorporated, New Taipei (TW); National Yang-Ming University, Taipei (TW)

(72) Inventors: Pei-Jung Chen, New Taipei (TW); Tsung-Hsien Tsai, New Taipei (TW); Liang-Kung Chen, Taipei (TW); Li-Ning Peng, Taipei (TW); Fei-Yuan Hsiao, Taipei (TW); Shih-Tsung Huang, Taipei (TW)

(73) Assignees: Acer Incorporated, New Taipei (TW); National Yang-Ming University, Taipei (TW)

( * ) Notice: Subject to any disclaimer, the term of this patent is extended or adjusted under 35 U.S.C. 154(b) by 808 days.

(21) Appl. No.: 16/843,917

(22) Filed: Apr. 9, 2020

(65) Prior Publication Data
US 2021/0265058 A1   Aug. 26, 2021

(30) Foreign Application Priority Data
Feb. 20, 2020   (TW) ................. 109105456

(51) Int. Cl.
*G16H 50/20*   (2018.01)
*A61B 5/00*   (2006.01)
(Continued)

(52) U.S. Cl.
CPC ........... *G16H 50/20* (2018.01); *A61B 5/4088* (2013.01); *A61B 5/4842* (2013.01);
(Continued)

(58) Field of Classification Search
CPC ................. G16H 50/20; G16H 10/60
See application file for complete search history.

(56) References Cited

U.S. PATENT DOCUMENTS

| | | | |
|---|---|---|---|
| 2008/0147441 A1* | 6/2008 | Kil .................. | G06Q 40/08 705/2 |
| 2019/0272922 A1* | 9/2019 | Albright ............... | G16H 50/70 |
| 2020/0303072 A1* | 9/2020 | Drokin ................. | G16H 10/60 |

FOREIGN PATENT DOCUMENTS

| CN | 106778014 | 5/2017 |
|---|---|---|
| CN | 107403072 | 11/2017 |

(Continued)

OTHER PUBLICATIONS

Yikuan Li and Shishir Rao (BEHRT: Transformer for Electronic Health Records, Jul. 24, 2019, arXiv: 1907.09538v1 [cs.LG] Jul. 22, 2019) (Year: 2019).*

(Continued)

*Primary Examiner* — Evangeline Barr
(74) *Attorney, Agent, or Firm* — JCIPRNET

(57) ABSTRACT

A training data processing method and an electronic device are provided. The method includes: obtaining medical history data including at least one first disease suffered by a user; setting a plurality of disease types according to a target disease; setting a time interval; obtaining at least one second disease in the time interval from the medical history data; performing a pre-processing operation on the second disease according to the disease types to obtain processed data; and inputting the processed data to a neural network to train the neural network.

8 Claims, 3 Drawing Sheets

(51) Int. Cl.
 *G16H 10/60* (2018.01)
 *G16H 50/50* (2018.01)
 *G16H 70/60* (2018.01)
(52) U.S. Cl.
 CPC ........... *A61B 5/7267* (2013.01); *G16H 10/60* (2018.01); *G16H 50/50* (2018.01); *G16H 70/60* (2018.01)

(56) References Cited

FOREIGN PATENT DOCUMENTS

| | | |
|---|---|---|
| CN | 109326353 | 2/2019 |
| TW | 201944429 | 11/2019 |
| WO | 2019168334 | 9/2019 |

OTHER PUBLICATIONS

Vijay S. Nori, et al., "Machine learning models to predict onset of dementia: A label learning approach." Alzheimer's & Dementia: Translational Research & Clinical Interventions, vol. 5, No. 1, Jan. 1, 2019, pp. 918-925.
Ji Hwan Park, et al., "Machine learning Prediction of Incidence of Alzheimer's Disease 3 Using Large-Scale Administrative Health Data." bioRxiv, Feb. 10, 2020, pp. 1-29.
Yikuan Li et al., "BEHRT: Transformer for Electronic Health Records", retrieved from arXiv database, arXiv: 1907.09538v1 [cs.LG], Jul. 22, 2019, pp. 1-17.
Shih-Tsung Huang et al., "Using Hypothesis-Led Machine Learning and Hierarchical Cluster Analysis to Identify Disease Pathways Prior to Dementia: Longitudinal Cohort Study", Journal of Medical Internet Research, Jul. 26, 2023, pp. 1-16, vol. 25, e41858.

\* cited by examiner

TRAINING DATA PROCESSING METHOD AND ELECTRONIC DEVICE

CROSS-REFERENCE TO RELATED APPLICATION

This application claims the priority benefit of Taiwan application serial no. 109105456, filed on Feb. 20, 2020. The entirety of the above-mentioned patent application is hereby incorporated by reference herein and made a part of this specification.

BACKGROUND

Technical Field

The disclosure relates to a training data processing method and an electronic device.

Description of Related Art

Regarding dementia and other similar diseases, diseases that a patient suffered from several years before the diagnosis of dementia or even earlier may be precursors of such dementia disease. Therefore, how to use historical data of diseases to predict whether it is possible for a patient to suffer from dementia is one of the problems to be resolved by a person of ordinary skill in the art.

SUMMARY

The disclosure provides a training data processing method and an electronic device capable of generating a more favorable prediction effect through an established neural network model compared to that provided by a conventional machine learning method.

The disclosure provides a training data processing method, used in an electronic device, the method includes the following steps. Medical history data including at least one first disease suffered by a user is obtained. A plurality of disease types are set according to a target disease. A time interval is set. At least one second disease in the time interval is obtained from the medical history data. A pre-processing operation is performed on the second disease according to the disease types to obtain processed data, and the processed data is inputted to a neural network to train the neural network.

The disclosure provides an electronic device including an input circuit and a processor. The input circuit obtains medical history data including at least one first disease suffered by a user. The processor sets a plurality of disease types according to a target disease. The processor sets a time interval. The processor obtains at least one second disease in the time interval from the medical history data. The processor performs a pre-processing operation on the second disease according to the disease types to obtain processed data. The processor inputs the processed data to a neural network to train the neural network.

Based on the above, the training data processing method and the electronic device of the disclosure are used to perform pre-processing on data used for training a model, so that a prediction effect of a neural network model established by using the processed data is more accurate than that provided by a conventional machine learning method. Further, an application scenario of the established model meets a real usage scenario.

DESCRIPTION OF THE EMBODIMENTS

A model training method of the disclosure is applicable to an electronic device (not shown). The electronic device includes an input circuit (not shown) and a processor (not shown). The input circuit is coupled to the processor. The input circuit is, for example, an input interface or a circuit configured to obtain related data from outside of the electronic device or other sources, which is not limited herein.

The processor may be a central processing unit (CPU), another programmable general-purpose or special-purpose microprocessor, a digital signal processor (DSP), a programmable controller, an application specific integrated circuit (ASIC), another similar element, or a combination of the foregoing elements.

In addition, the electronic device may further include a storage circuit (not shown). The storage circuit may be a fixed or removable random access memory (RAM) in any form, a read-only memory (ROM), a flash memory, a similar element, or a combination of the foregoing elements.

In an exemplary embodiment, the storage circuit of the electronic device stores a plurality of code snippets. After being installed, the code snippets are performed by the processor. For example, the storage circuit includes a plurality of modules, and operations applied to the electronic device are respectively performed by using the modules. The modules are formed by one or more code snippets, but the disclosure is not limited thereto. The operations of the electronic device may also be implemented in a manner of another hardware form.

Figure 1:
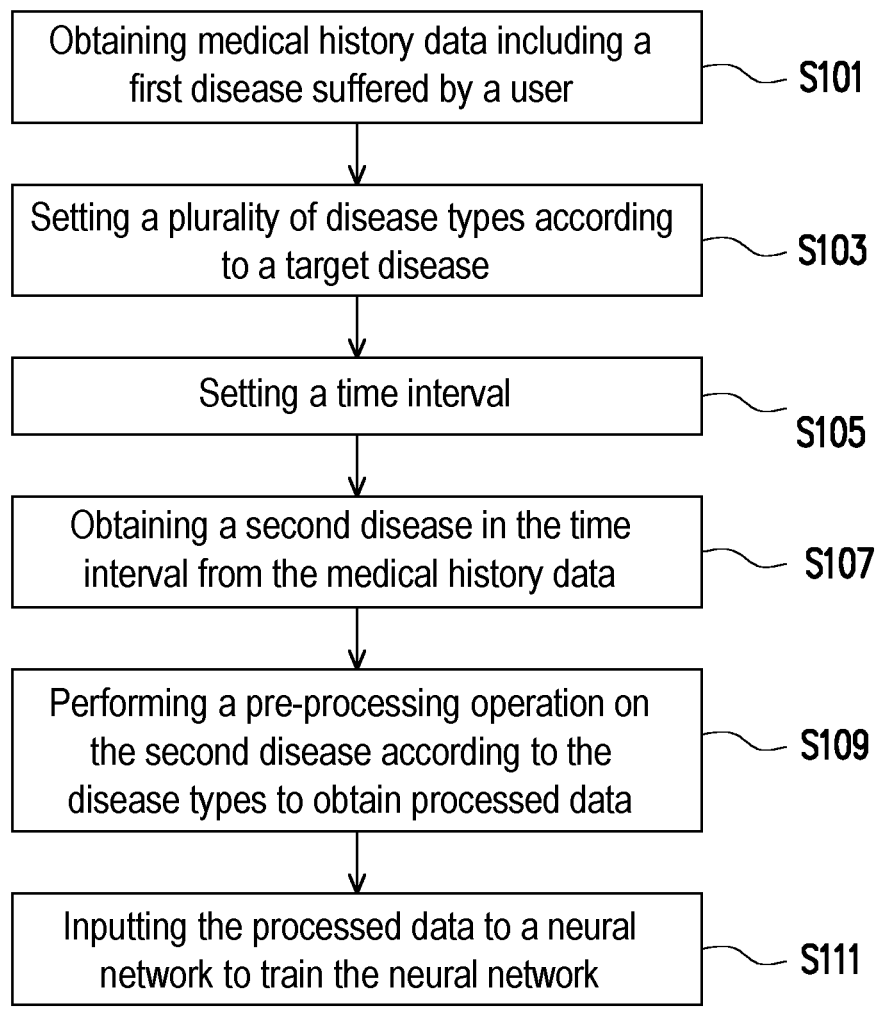
FIG. 1 is a schematic chart of a training data processing method according to an embodiment of the disclosure.

FIG. 1 is a schematic chart of a training data processing method according to an embodiment of the disclosure. Particularly, a model (or a neural network) trained by using the disclosure may be used for predicting whether a subject may suffer from a target disease or a probability of having the target disease.

Specifically, referring to FIG. 1, first, an input circuit obtains medical history data including a disease (also referred to as a first disease) suffered by a user (step S101). Then, the processor sets a plurality of disease types according to a target disease (step S103). The target disease is exemplified as dementia for description below, but the types of the target disease is not limited in the disclosure.

More specifically, the processor converts a plurality of types of predetermined diseases into a plurality of types of data (or a plurality of types). The processor selects, according to a to-be-predicted target disease, disease types corresponding to an appropriate number of diseases that are highly related in the medical field. For example, the processor may perform screening (for example, deleting or adding some diseases) in the plurality of types of data according to the to-be-predicted target disease to obtain disease types finally used in step S103. It should be noted that, when the number of the disease types is excessively small, disease information may be insufficient to predict the target disease, and when the number of the disease types is excessively large, noise increases, and prediction accuracy is thus lowered.

For example, assuming that the target disease is dementia, the processor may select a disease classification of CCS single level diagnoses, which includes 285 types of diseases. The processor may set disease types corresponding to the 258 types of diseases in step S103.

After step S101 is performed, the processor sets a time interval (step S105) and obtains a second disease in the time interval from the medical history data (step S107). The processor performs a pre-processing operation on the second disease according to the disease types to obtain processed data (step S109). Finally, the processor inputs the processed data to a neural network to train the neural network (step S111).

Figure 2A:
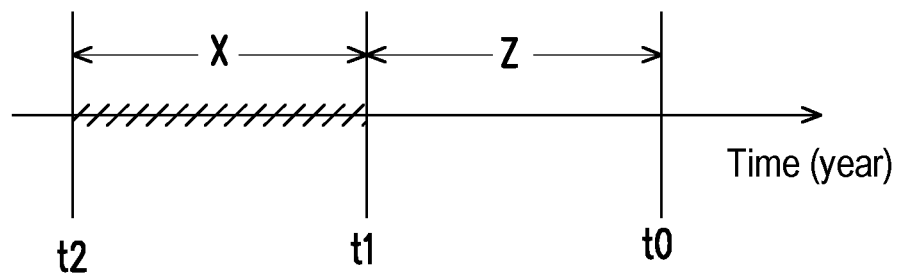
FIG. 2A and FIG. 2B are schematic diagrams illustrating time intervals according to an embodiment of the disclosure.
Figure 2B:
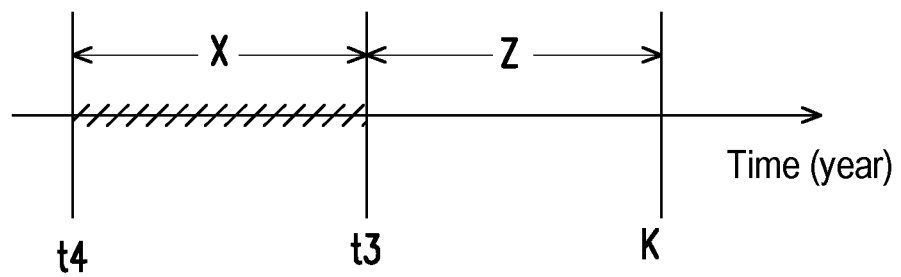

For example, FIG. 2A and FIG. 2B are schematic diagrams illustrating time intervals according to an embodiment of the disclosure. It should be noted that, the user to which the medical history data obtained in step S101 belongs may suffer from the target disease or not suffer from the target disease. For the two different types of users, different manners may be used to obtain the second disease in the time interval.

For example, referring to FIG. 2A, FIG. 2A is an example describing how to define a time interval used for obtaining the second disease from the medical history data of the user suffering from the target disease. As shown in FIG. 2A, a time point t0 is, for example, a time point when the user has (or is first diagnosed with) the target disease, a time point t1 (also referred to as a first time point) is Z years from the time point t0 (namely, the time point t1 is Z years ago before the time point t0), and a time point t2 (also referred to as a second time point) is X years from the time point t1 (namely, the time point t2 is X years ago before the time point t1), where Z and X are positive numbers. In such a design, a time unit may be several years or months or the like as required by actual scenarios. The time interval used for obtaining the second disease in FIG. 2A is between the time point t1 and the time point t2.

In addition, referring to FIG. 2B, FIG. 2B is an example describing how to define a time interval used for obtaining the second disease from the medical history data of a user not suffering from the target disease. As shown in FIG. 2B, a time point k is, for example, a time point when the medical history data of the user is obtained, a time point t3 (also referred to as a third time point) is Z years from the time point k (namely, the time point t3 is Z years ago before the time point k), and a time point t4 (also referred to as a fourth time point) is X years from the time point t3 (namely, the time point t4 is X years ago before the time point t3), where Z and X are positive numbers. In such a design, a time unit may be several years or months or the like as required by actual scenarios. The time interval used for obtaining the second disease in FIG. 2B is between the time point t3 and the time point t4. However, it should be noted that, in other embodiments, the time point t3 may be any other time point earlier than the time point k.

It should be noted that, the time intervals are defined in the foregoing manner because if an observation starting point (for example, the time point t1) is excessively early, the user suffering from the target disease may not show a physical difference yet, so the medical history cannot be used for establishing a model and for prediction, and if the observation starting point (for example, the time point t1) is excessively late, even if the prediction succeeds, the user is close to the time of being diagnosed with the target disease, and the effect of target disease prevention is not achieved. In the present embodiment, since the target disease is dementia, the processor may set the Z value to 5 and set the X value to 1. That is, by using the example of FIG. 2A, the time interval is between five years and six years ago before the time point t0 when the user has dementia.

How to obtain the second disease in the time interval from the medical history data is described herein. Herein, two manners are used: (1) a disease sequence; and (2) word frequency information. The two different manners are described below respectively.

[Disease Sequence]

Two types of manners may be used to generate the disease sequence. In an embodiment, the processor finds diseases in the time interval from diseases (namely, first diseases) in the medical history data according to earliest occurrence times of the diseases and finds a disease sequence formed by at least one disease (also referred to as the second diseases) from the diseases in the time interval. Particularly, the second diseases in the disease sequence are sorted according to the earliest occurrence times, a number of the second diseases is less than or equal to a predetermined number, and each of the second diseases only occurs once.

For example, it is assumed that the predetermined number is 5, and it is assumed that a sequence of diagnosed diseases of a person (or diseases that the person suffers from) in the medical history in the time interval is "disease 2→disease 2→disease 1→disease 2→disease 4→disease 3→disease 3". If sorting is performed by using the earliest occurrence times, a disease sequence of "disease 2→disease 1→disease 4→disease 3" may be obtained. In the sequence, the number of diseases (namely, 4) is less than the predetermined (namely, 5). Further, in the disease sequence, each disease only occurs once.

In the second manner, according to all occurrence times of the diseases in the medical history data, the processor finds diseases in the time interval from the diseases, and sorts the diseases according to the occurrence time sequence. The diseases in the disease sequence generated in this manner may be repeated.

In addition, in an embodiment, the processor deletes some diseases (also referred to as third diseases) in the medical history data to obtain a disease sequence formed by a plurality of diseases (for example, the second diseases). Occurrence times of the third diseases are earlier than occurrence times of the diseases in the disease sequence. The diseases in the disease sequence are sorted according to the earliest occurrence times, and the number of the diseases in the disease sequence is less than or equal to a predetermined number.

For example, it is assumed that the predetermined number is 5 and assumed that the second manner is used. A sequence of diagnosed diseases of a person or diseases that the person suffers from in the medical history in the time interval is "disease 2→disease 2→disease 1→disease 2→disease 4→disease 3→disease 3". Because the number (namely, 7) of the diseases (or diagnosed diseases) in the medical history data is greater than the predetermined number, the processor may, for example, delete the diseases "disease 2→disease 2" occurring earlier in the medical history data, and that the disease sequence of "disease 1→disease 2→disease 4→disease 3→disease 3" is obtained.

After the second diseases in the time interval are obtained in the foregoing manner, the second diseases in the disease sequence may be encoded as one-dimensional or two-dimensional encoded data (or referred to as a vector) according to the disease types in step S109, the encoded data is treated as processed data, and the processed data is input to a neural network to train the neural network in step S111.

Herein, an example in which the second diseases are encoded as one-dimensional encoded data is used for description. It is assumed that there are five disease types, and "disease 1", "disease 2", "disease 3", "disease 4", and "disease 5" are respectively defined as "[1,0,0,0,0]", "[0,1,0,0,0]", "[0,0,1,0,0]", "[0,0,0,1,0]", and "[0,0,0,0,1]". Assuming that the disease sequence obtained in the foregoing manner is "disease 2→disease 1→disease 4→disease 3". The processor may convert the disease sequence into: "[0, 1,0,0,0]→[1,0,0,0,0]→[0,0,0,1,0]→[0,0,1,0,0]" and further generates one-dimensional data "[0,1,0,0,0, 1,0,0,0,0, 0,0,0,1,0, 0,0,1,0,0]". Then, the one-dimensional data may be inputted to a neural network using one-dimensional data as input.

Herein, an example in which the second diseases are encoded as two-dimensional encoded data is used for description. It is assumed that there are five disease types, and "disease 1", "disease 2", "disease 3", "disease 4", and "disease 5" are respectively defined as "[1,0,0,0,0]", "[0,1,0,0,0]", "[0,0,1,0,0]", "[0,0,0,1,0]", and "[0,0,0,0,1]". Assuming that the disease sequence obtained in the foregoing manner is "disease 2→disease 1→disease 4→disease 3". The processor may convert the disease sequence into: "[0, 1,0,0,0] →[1,0,0,0,0] →[0,0,0,1,0] →[0,0,1,0,0]" and further generates two-dimensional data as the following matrix:

$$\begin{bmatrix} 0 & 1 & 0 & 0 & 0 \\ 1 & 0 & 0 & 0 & 0 \\ 0 & 0 & 0 & 1 & 0 \\ 0 & 0 & 1 & 0 & 0 \end{bmatrix}$$

Next, the two-dimensional data may be inputted to a neural network (for example, LSTM) using two-dimensional data as input.

Particularly, since the one-dimensional or two-dimensional data encodes the diseases according to a time sequence, the encoded data still retains a sequence relationship between the diseases.

In a process of training the neural network, for example, a length of the converted vector may be set to M by using a sentence embedding method, and the vector may be trained together with the neural network (for example, LSTM).

[Word Frequency Information]

Figure 3:
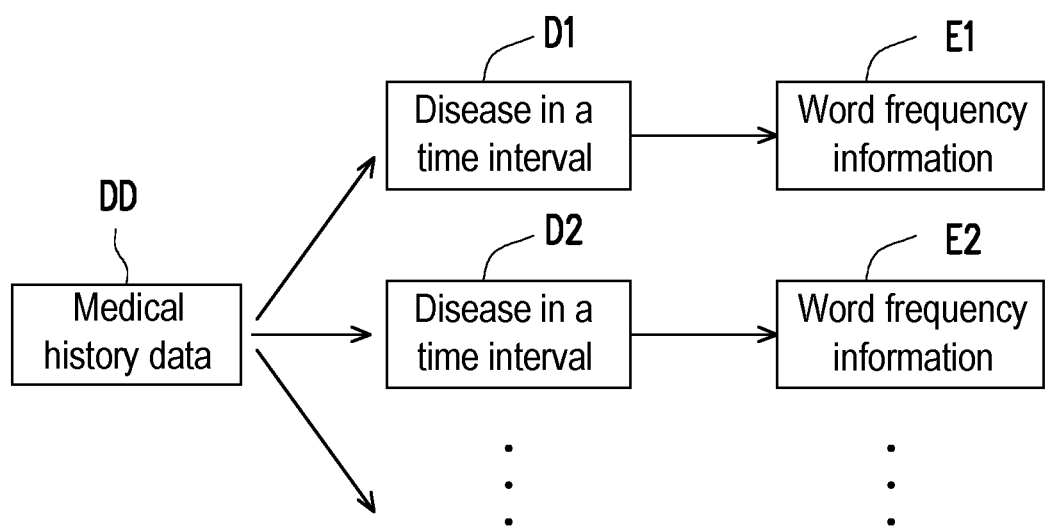
FIG. 3 is a schematic diagram illustrating generation of word frequency information according to an embodiment of the disclosure.

FIG. 3 is a schematic diagram illustrating generation of word frequency information according to an embodiment of the disclosure.

Referring to FIG. 3, in an embodiment, the processor may directly take diseases D1 to D2 in the time interval from medical history data DD as the second diseases forming the disease sequence. After weighting the diseases D1 to D2 (weights are not limited herein), the processor treats the diseases as words and respectively converts the words into word frequency information E1 to E2 by using a TF-IDF algorithm.

It should be noted that, how to weight the diseases is not limited in the disclosure. In an embodiment, the diseases may be weighted based on whether the diseases have been diagnosed. For example, a weight of a diagnosed disease may be set to 1, or otherwise, the weight=0.

In another embodiment, the diseases may be weighted based on a number of visits for the diseases. Assuming that a medical history of a person is: "disease 2→disease 2→disease 1→disease 2→disease 4→disease 3→disease 3". In this way, a weighted value of the disease 1 of the person is 1, a weighted value of the disease 2 is 3, a weighted value of the disease 3 is 2, and a weighted value of the disease 4 is 1.

In another embodiment, the diseases may be weighted based on other medical history information. Other medical history data includes: individual disease dosages, surgery information, symbolic chronic diseases, other treatments, and the like, which are not limited herein.

In another embodiment, the diseases may also be weighted by using disease dosages. Assuming that three persons A, B, and C have once been diagnosed with diabetes with the dosages of 2 units, 1 unit, and 3 units respectively. In this manner, weights of diabetes of the three persons are respectively 2, 1, and 3.

In another embodiment, disease importance may also be first sorted through another machine learning method, and then the diseases are weighted by using the disease importance.

After the weighted second diseases are respectively converted into word frequency information, the processor treats the word frequency information as processed data and inputs the processed data to a neural network to train the neural network. Particularly, a format of the word frequency information usually meets a general machine learning input data format, and therefore may be directly input to the neural network for training.

After the neural network is trained completely through the foregoing manner, when the neural network receives medical history data of a subject, whether the subject may be diagnosed with the target disease (for example, dementia) or a probability of having the target disease is determined by using the neural network.

Based on the above, the training data processing method and the electronic device of the disclosure are used to perform pre-processing on data used for training a model, so that the prediction effect of a neural network model established by using the processed data is more favorable than that provided by a conventional machine learning method. Moreover, an application scenario of the established model meets a real usage scenario.

What is claimed is:

1. A training data processing method, used in an electronic device, the electronic device includes a flash memory, the training data processing method comprising:

obtaining, by the flash memory, medical history data comprising at least one first disease suffered by a user;

setting, by the flash memory, a plurality of disease types according to a target disease;

setting, by the flash memory, a time interval, wherein the user does not suffer from the target disease, wherein the time interval is between a third time point and a fourth time point, the third time point is Z years ago before a time point, wherein the time point is when the medical history data is obtained, the fourth time point is X years ago before the third time point, and Z and X are positive numbers;

obtaining, by the flash memory, at least one second disease in the time interval from the medical history data;

performing, by the flash memory, a pre-processing operation on the at least one second disease according to the disease types to obtain processed data;

inputting, by the flash memory, the processed data to a neural network to train the neural network;

receiving, by the trained neural network, the medical history data of a subject; and determining, by the trained neural network, whether the subject will be diagnosed with the target disease, wherein a prediction effect of the trained neural network is enhanced by training with the processed data, wherein the step of performing the pre-processing operation on the at least one second disease according to the disease types to obtain the processed data comprises:

encoding, by the flash memory, the at least one second disease in a disease sequence as one-dimensional or two-dimensional encoded data according to the disease types and using the encoded data as the processed data, wherein a length of the encoded data is set by a sentence embedding method, and the encoded data is trained together with the neural network;

weighting, by the flash memory, each of the at least one second disease; and respectively converting, by the flash memory, the weighted at least one second disease into at least one piece of word frequency information by using a TF-IDF algorithm and treating the word frequency information as the processed data.

2. The training data processing method according to claim 1, wherein the user suffers from the target disease, the time interval is between a first time point and a second time point, the first time point is Z years ago before a time point when the user is diagnosed with the target disease, the second time point is X years ago before the first time point, and Z and X are positive numbers.

3. The training data processing method according to claim 1, wherein the step of obtaining the at least one second disease in the time interval from the medical history data comprises:

obtaining, by the flash memory, the disease sequence formed by the at least one second disease from the at least one first disease according to an earliest occurrence time of each of the at least one first disease, wherein the at least one second disease in the disease sequence is sorted according to the earliest occurrence time, a number of the at least one second disease is less than or equal to a predetermined number, and each of the at least one second disease only occurs once.

4. The training data processing method according to claim 1, wherein the step of obtaining the at least one second disease in the time interval from the medical history data comprises:

deleting, by the flash memory, at least one third disease in the medical history data to obtain the disease sequence formed by the at least one second disease, wherein an occurrence time of the third disease is earlier than an occurrence time of the at least one second disease, the at least one second disease in the disease sequence is sorted according to an earliest occurrence time, and a number of the at least one second disease is less than or equal to a predetermined number.

5. An electronic device, comprising:
an input circuit; and
a flash memory, coupled to the input circuit, wherein
the input circuit obtains medical history data comprising at least one first disease suffered by a user,
the flash memory sets a plurality of disease types according to a target disease,
the flash memory sets a time interval, wherein the user does not suffer from the target disease, wherein the time interval is between a third time point and a fourth time point, the third time point is Z years ago before a time point, wherein the time point is when the medical history data is obtained, the fourth time point is X years ago before the third time point, and Z and X are positive numbers, the flash memory obtains at least one second disease in the time interval from the medical history data, the flash memory performs a pre-processing operation on the second disease according to the disease types to obtain processed data, the flash memory inputs the processed data to a neural network to train the neural network, the trained neural network receives the medical history data of a subject, and the trained neural network determines whether the subject will be diagnosed with the target disease, wherein a prediction effect of the trained neural network is enhanced by training with the processed data, wherein in the operation of performing the pre-processing operation on the at least one second disease according to the disease types to obtain the processed data, the flash memory encodes the at least one second disease in a disease sequence as one-dimensional or two-dimensional encoded data according to the disease types and uses the encoded data as the processed data, wherein a length of the encoded data is set by a sentence embedding method, and the encoded data is trained together with the neural network, the flash memory weights each of the at least one second disease, and the flash memory respectively converts the weighted at least one second disease into at least one piece of word frequency information by using a TF-IDF algorithm and treats the word frequency information as the processed data.

6. The electronic device according to claim 5, wherein the user suffers from the target disease, the time interval is between a first time point and a second time point, the first time point is Z years ago before a time point when the user is diagnosed with the target disease, the second time point is X years ago before the first time point, and Z and X are positive numbers.

7. The electronic device according to claim 5, wherein in the operation of obtaining the at least one second disease in the time interval from the medical history data, the flash memory obtains the disease sequence formed by the at least one second disease from the at least one first disease according to an earliest occurrence time of each of the at least one first disease, wherein the at least one second disease in the disease sequence is sorted according to the earliest occurrence time, a number of the at least one second disease is less than or equal to a predetermined number, and each of the at least one second disease only occurs once.

8. The electronic device according to claim 5, wherein in the operation of obtaining the at least one second disease in the time interval from the medical history data, the flash memory deletes at least one third disease in the medical history data to obtain the disease sequence formed by the at least one second disease, wherein an occurrence time of the third disease is earlier than an occurrence time of the at least one second disease, the at least one second disease in the disease sequence is sorted according to an earliest occurrence time, and a number of the at least one second disease is less than or equal to a predetermined number.

* * * * *